US00PP14137P39

(12) United States Plant Patent
Manichote

(10) Patent No.: US PP14,137 P3
(45) Date of Patent: Sep. 16, 2003

(54) AGLAONEMA PLANT NAMED 'DYNAMIC RUBY'

(75) Inventor: Pichai Manichote, Bangkok (TH)

(73) Assignee: Ladda Co., Ltd. (TH)

( * ) Notice: Subject to any disclaimer, the term of this patent is extended or adjusted under 35 U.S.C. 154(b) by 0 days.

(21) Appl. No.: 09/995,069

(22) Filed: Nov. 27, 2001

(65) Prior Publication Data

US 2003/0101500 P1 May 29, 2003

(51) Int. Cl.[7] ..... A01H 5/00

(52) U.S. Cl. ..... Plt./376

(58) Field of Search ..... Plt./376

*Primary Examiner*—Bruce R. Campell
*Assistant Examiner*—Anne Marie Grünberg
(74) *Attorney, Agent, or Firm*—Christie, Parker & Hale, LLP

(57) ABSTRACT

A new and distinct cultivar of Aglaonema named 'Dynamic Ruby' characterized by its light red mottles on green ovate leaves, compact and well-branched growth habit.

3 Drawing Sheets

Botanical classification: The botanical classification of the new variety is *Aglaonema* (*rotundum* 'Giant'×*tenuipes*)× *Aglaonema brevispathum* 'Dynamic Ruby'.

BACKGROUND OF THE INVENTION

The present invention is directed to a new and distinct variety of Aglaonema, botanically known as *Aglaonema* (*rotundum* 'Giant'×*tenuipes*)×*Aglaonema brevispathum*. The varietal denomination of the new variety is 'Dynamic Ruby.'

The new variety was a seedling among a progeny of *Aglaonema* (*rotundum* 'Giant'×*tenuipes*)×*Aglaonema brevispathum,* selected by the inventor.

Asexual propagation of the new variety in Nakhon Pathom, Thailand by vegetative cuttings has demonstrated the uniformity and the stability through successive generations of this new Aglaonema.

SUMMARY OF THE INVENTION

The following traits have been repeatedly observed in the new variety grown from top cutting under 50% shade conditions in Nakhon Pathom, Thailand which closely approximate those commonly used in commercial horticultural practice.

The features that in combination are believed to distinguish the new variety from other known varieties of Aglaonema include: compact growth habit with freely branching, dense and upright growth; ovate leaves; adaxial leaf surfaces having dark green color with light red mottles.

COMPARISON WITH OTHER VARIETY

Plants of the new Aglaonema can be compared to plants of the Aglaonema 'Siam Majesty' (U.S. Plant Pat. No. 13,141, Filed: Nov. 6, 2000). Plants of the new Aglaonema differ from plants of 'Siam Majesty' by the following combination of characteristics:

1. Whereas the adaxial leaf surfaces of the new variety have light red mottles instead of plain green as found in 'Siam Majesty';

2. The mid-rib and veins of the new variety are green instead of red as found in 'Siam Majesty'; and
3. The leaf tip of the new variety is attenuate while that of the 'Siam Majesty' is acuminate.

Plants of the new Aglaonema may be compared to its parents. Plants of the new Aglaonema differ from female parent, the unpatented *Aglaonema* (*rotundum* 'Giant'× *tenuipes*) which commonly grown in Thailand, by the following combination of characteristics:

1. The adaxial leaf surfaces of the new variety have light red mottles on green surface with green midrib instead of plain green surface with red midrib as found in the female parent;
2. The leaf tip of the new variety is attenuate while that of the female parent is acuminate.

Plants of the new Aglaonema differ from plants of *Aglaonema brevispathum* (unpatented), which commonly grown in Thailand the male parent, by the following combination of characteristics:

1. The adaxial leaf surfaces of the new variety have light red mottles on green surface instead of white mottles on green surface as found in the male parent;
2. The leaf of the new variety is ovate while that of the male parent is lanceolate.

BRIEF DESCRIPTION OF ILLUSTRATIONS

The accompanying photographs show the overall appearance of the new variety as nearly correct as it is possible to make in a color illustration of this type. Throughout this specification, color values are based upon the of The Royal Horticultural Society Colour Chart except where common terms of color definition are employed.

FIG. 1 shows a top view of a single plant of 'Dynamic Ruby' in a 30 cm container about 15 months after planting;

FIG. 2 shows a view of the adaxial surface of a mature leaf of the new variety; and FIG. 3 shows the comparison between the adaxial leaf surface of 'Dynamic Ruby' and its comparison variety 'Siam Majesty'.

DESCRIPTION OF THE NEW VARIETY

All color references are in accordance with The Royal Horticultural Society Colour Chart. (1995 edition) Colors are approximate as color depends on climate and environmental condition. Phonotypic expression may vary with environmental, cultural and climatic conditions, as well as differences in conditions of light and soil.

Botanical classification: Aglaonema hybrids 'Dynamic Ruby'.

Parentage:

*Female parent.*—*Aglaonema* (*rotundum*×*tenuipes*).

*Male parent.*—*Aglaonema brevispathum.*

Propagation: By top cuttings, stem cuttings and by division. Root initiation: within 3.5 week. No fruit setting (sexually sterile).

Plant:

*Shape.*—Upright and outwardly Spreading, symmetrical, dense and compact.

*Growth habit.*—Erect when young, becoming more outwardly arching and spreading as plant develops.

*Size.*—Height from soil surface to top of leaf canopy about 20 to 29 cm; width about 25 to 33 cm.

*Vigor.*—Vigorous, rapid growth rate.

Foliage:

*Leaf.*—Venation: Pinnate, strongly differentiated into 5 pairs of primary vein, diverging from midrib at 60–75°.

*Length of bloom time.*—2–3 days.

*Time of bloom.*—December–February.

*Disease resistance.*—Not evaluated.

*Shape.*—Ovate with an attenuate apex, an obtuse base and entire margin; symmetric leaf blade.

*Size.*—Length about 14.6 to 20.2 cm; width about 7.9 to 9.3 cm.

*Surface.*—Smooth and waxy.

*Aspect.*—Erect initially, eventually horizontal to the stem.

*Petiole.*—Length about 2.2 to 3.3 cm.

*Color.*—

*Young.*—Upper surface near 137D, mottles, near 52A; mid-rib and veins near 145B; lower surface near 137D, mottles near 36C, mid-rib and veins near 145D.

*Mature.*—Upper surface near 137C, mottles near 56A, mid-rib and veins near 137A; lower surface near 137C, mottles near 36A, mid-rib veins near 137C.

*Inflorescence.*—Typical of Aglaonema.

Peduncle solitary length 4–9 cm.; spathe gibbons length 5.5 cm. and 2.8 cm wide, often apiculate near 143A; spadix clavate to 4.5 cm. long and 1 cm. in diameter; pistillate portion with 17 pistils near 49B, sweet scent; stigma near 13A; ovary near 49B; no staminode; staminate portion 3.5 cm. long and 1 cm. thick near 155D, flower bud length 5.2 cm. near 143C.

Plants of the Aglaonema cultivar 'Dynamic Ruby' are dense compact and have upright growth habit. The upper leaf surface are green with light red mottles. The leaves are ovate in shape with attenuate apex. White storage roots are present.

I claim:

1. A new and distinct variety of Aglaonema plant named 'Dynamic Ruby' substantially as illustrated and described herein.

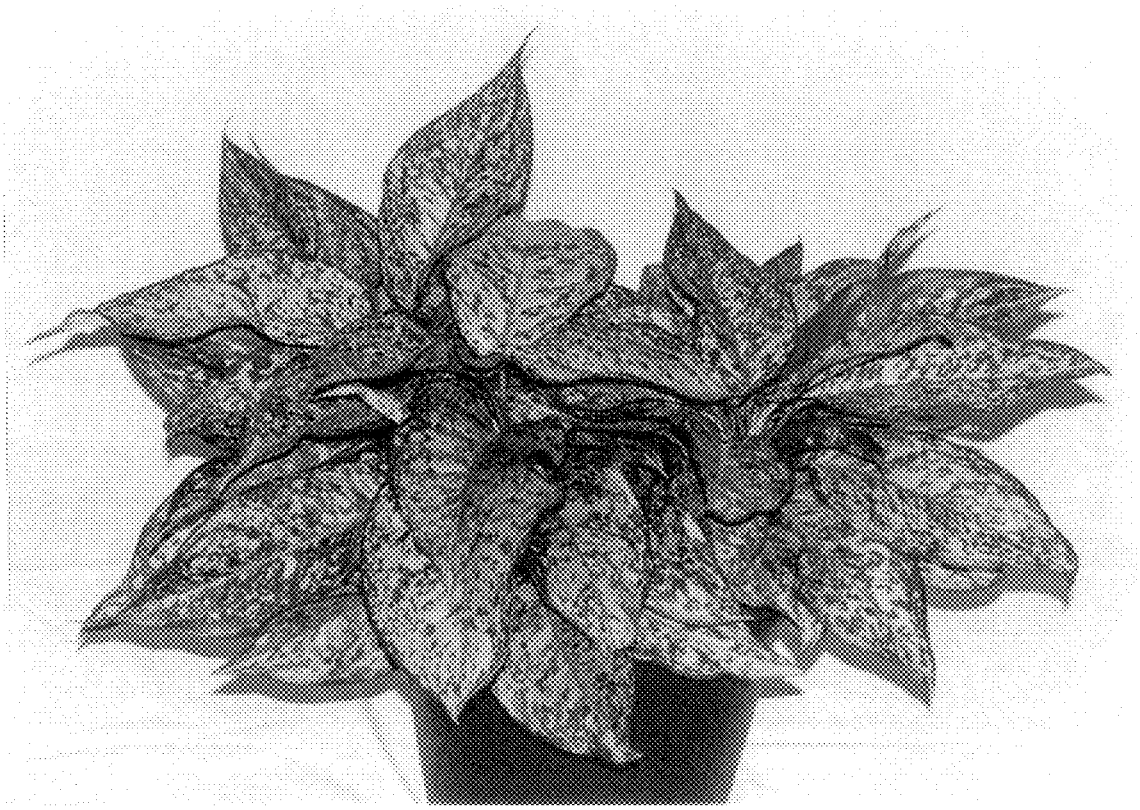

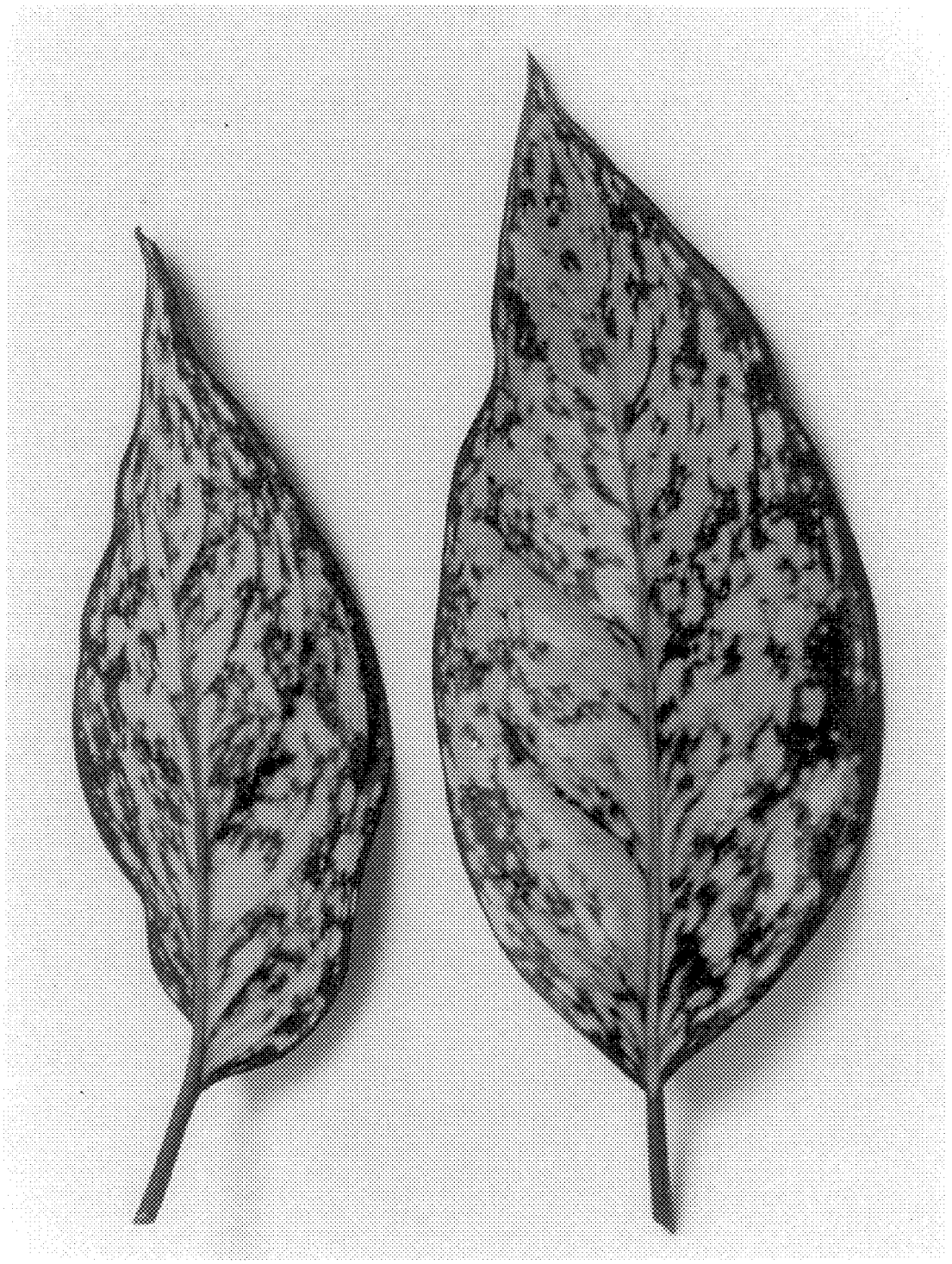

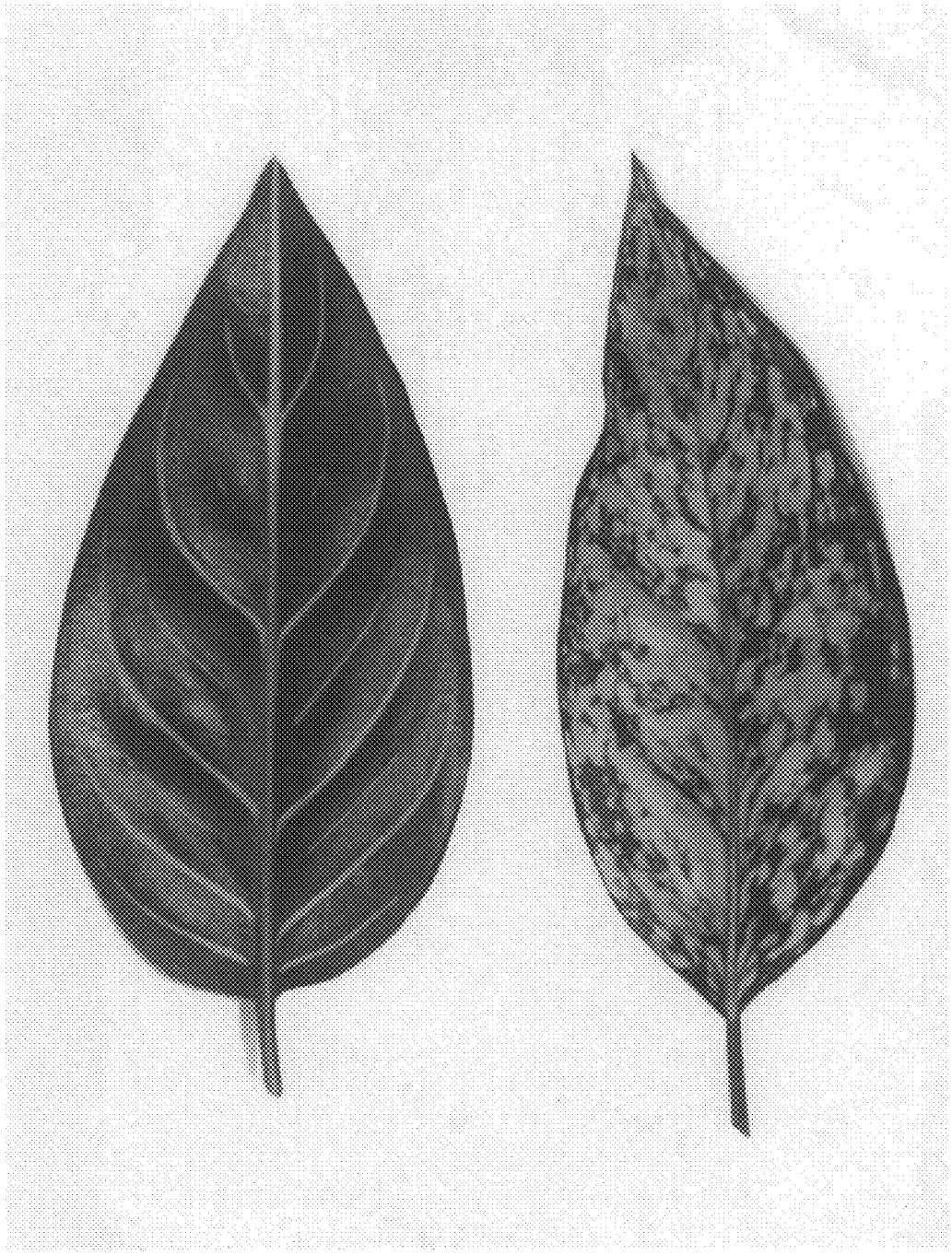

* * * * *